US012576180B2

(12) United States Patent
Lundman et al.

(10) Patent No.: US 12,576,180 B2
(45) Date of Patent: Mar. 17, 2026

(54) ABSORBENT ARTICLE WITH PLANT PROTEIN BASED ABSORBENT MATERIAL

(71) Applicant: Essity Hygiene and Health Aktiebolag, Gothenburg (SE)

(72) Inventors: Malin Lundman, Gothenburg (SE); Antonio Capezza, Spånga (SE); Eva Johansson, Veberöd (SE); William Roy Newson, Åkarp (SE); Mikael Hedenqvist, Nacka (SE); Richard Olsson, Lidingö (SE); Shabira Abbas, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 818 days.

(21) Appl. No.: 17/618,115

(22) PCT Filed: Jun. 13, 2019

(86) PCT No.: PCT/EP2019/065473
§ 371 (c)(1),
(2) Date: Dec. 10, 2021

(87) PCT Pub. No.: WO2020/249214
PCT Pub. Date: Dec. 17, 2020

(65) Prior Publication Data
US 2022/0296768 A1 Sep. 22, 2022

(51) Int. Cl.
*A61L 15/42* (2006.01)
*A61L 15/40* (2006.01)
(52) U.S. Cl.
CPC .............. *A61L 15/40* (2013.01); *A61L 15/42* (2013.01)

(58) Field of Classification Search
CPC ................ A61F 13/15203; A61F 13/53; A61F 2013/530481; C08L 89/00; C08L 1/00;
(Continued)

(56) References Cited

U.S. PATENT DOCUMENTS 5,801,116 A    9/1998 Cottrell et al.
5,847,089 A    12/1998 Damodaran et al.
(Continued)

FOREIGN PATENT DOCUMENTS

CN        1244388 A     2/2000
CN        101074300 A   11/2007
(Continued)

OTHER PUBLICATIONS

Wu, Q. et al. "Highly Absorbing Antimicrobial Biofoams Based on Wheat Gluten and its Biohybrids" ACS Sustainable Chem. Eng. 2016, vol. 4, No. 4, pp. 2395-2404.
(Continued)

*Primary Examiner* — Leslie R Deak
*Assistant Examiner* — Seth Han
(74) *Attorney, Agent, or Firm* — BUCHANAN INGERSOLL & ROONEY PC

(57) ABSTRACT

An absorbent article for absorption of body fluids, including an absorbent member that includes at least one plant protein based absorbent material obtainable by a method including the steps of i. providing a mixture or suspension including a liquid and a plant protein, wherein the plant protein is insoluble in the liquid, ii. acylating the plant protein by adding an acylating agent thereto, and iii. obtaining the plant protein based absorbent material.

21 Claims, 8 Drawing Sheets

(58) Field of Classification Search

CPC .... C08L 1/02; C08L 3/04; C08L 33/08; C08L 5/00; C08L 5/04; C08L 5/08; C08L 89/06

See application file for complete search history.

(56) References Cited

U.S. PATENT DOCUMENTS

| | | | |
|---|---|---|---|
| 5,922,379 | A | 7/1999 | Wang |
| 6,033,769 | A | 3/2000 | Brueggemann |
| 6,608,237 | B1 * | 8/2003 | Li ..................... A61F 13/15203 604/382 |
| 6,821,331 | B2 | 11/2004 | Damodaran |
| 6,841,644 | B2 | 1/2005 | Phillips et al. |
| 8,329,601 | B2 | 12/2012 | Shi et al. |
| 8,466,337 | B2 | 6/2013 | Wang et al. |
| 8,785,417 | B2 | 7/2014 | Couffin et al. |
| 9,643,157 | B2 | 5/2017 | Joshi et al. |
| 2004/0200386 | A1 * | 10/2004 | Damodaran ............ A61L 15/60 106/140.3 |
| 2006/0065159 | A1 | 3/2006 | Oyasato |
| 2006/0135920 | A1 | 6/2006 | Virgilio et al. |
| 2010/0057027 | A1 | 3/2010 | Furno et al. |
| 2010/0266743 | A1 | 10/2010 | Chen et al. |
| 2015/0250919 | A1 * | 9/2015 | Kettlewell ........ A61F 13/00987 252/194 |
| 2018/0000662 | A1 * | 1/2018 | Chmielewski .......... A61L 15/62 |
| 2018/0085486 | A1 * | 3/2018 | Chen ..................... A61L 15/225 |
| 2018/0139933 | A1 | 5/2018 | Akeso |
| 2018/0344537 | A1 * | 12/2018 | Kurihara ................. A61L 15/60 |

FOREIGN PATENT DOCUMENTS

| | | | |
|---|---|---|---|
| CN | 101888789 | A | 11/2010 |
| CN | 107432956 | A | 12/2017 |
| CO | 4340610 | A1 | 7/1996 |
| EP | 1466630 | A1 | 10/2004 |
| ES | 2371249 | T3 | 12/2011 |
| JP | 2004536624 | A | 12/2004 |
| KR | 20160049682 | A | 5/2016 |
| NZ | 520632 | A | 2/2004 |
| WO | 9640817 | A1 | 12/1996 |
| WO | WO-0141866 | A1 * | 6/2001 ........... A61N 1/0573 |
| WO | 0160921 | A1 | 8/2001 |
| WO | 2005084724 | A1 | 9/2005 |

OTHER PUBLICATIONS

Questr, S. et al."Towards gliadin nanofoams" Colloid Polym Sci, (2017), vol. 295, pp. 267-275.

International Preliminary Report on Patentability and Written Opinion issued in corresponding International Application No. PCT/EP2019/065473 dated Dec. 14, 2021.

Office Action (Notification of the First Office Action) issued on Apr. 15, 2022 by the National Intellectual Property Administration (CNIPA) of the People's Republic of China in corresponding Chinese Patent Application No. 201980097466.9, and an English Translation of the Office Action. (21 pages).

Hwang, Der-Chyan, et al., "Chemical Modification Strategies for Synthesis of Protein-Based Hydrogel", Journal of Agricultural and Food Chemical, Mar. 1, 1996, pp. 751-768, vol. 44, No. 3, XP-002166719, American Chemical Society, Books and Journals Divisional, US. (8 pages).

International Search Report (PCT/ISA/210) and Written Opinion (PCT/ISA/237) mailed on Feb. 20, 2020, by the European Patent Office as the International Searching Authority for International Application No. PCT/EP2019/065473. (11 pages).

Office Action issued on May 2, 2024, by the Mexican Patent Office in corresponding Mexican Patent Application No. MX/a/2021/015259, and a machine English Translation of the Office Action. (8 pages).

Office Action issued on May 24, 2024, by the Colombian Patent Office in corresponding Colombian Patent Application No. NC2021/0017386, and a machine English Translation of the Office Action. (23 pages).

Office Action issued on Jan. 7, 2025, by the Colombian Patent Office in corresponding Colombian Patent Application No. NC2021/0017386, and a machine English Translation of the Office Action. (30 pages).

* cited by examiner

ABSORBENT ARTICLE WITH PLANT PROTEIN BASED ABSORBENT MATERIAL

FIELD OF THE INVENTION

The technology proposed herein relates to the field of absorbent articles with an absorbent member comprising plant protein based absorbent materials, providing alternatives to conventional (petroleum based) absorbent materials.

BACKGROUND

Absorbent materials are used in a wide range of applications where the material's capacity of absorbing and retaining large amounts of fluids, primarily water, blood or other bodily fluids provide functional benefits. Applications include disposable absorbent products, such as medical dressings and hygiene articles, for example diapers, incontinence pads, sanitary napkins, tampons and the like.

While many materials such as tissue paper, cotton and cellulose pulp absorb moderate amounts of water, the absorbing capacity is limited and these materials tend to shed the absorbed water if compressed.

Accordingly, various petroleum based absorbent materials are known, where some are fully petroleum based, such as for example obtained by polymerizing a blend of acrylic acid whereas other materials are partly petroleum based, being formed by grafting acrylonitrile polymers onto a backbone of, for example, starch.

Due to the nature of the products utilizing these absorbent materials, in many cases being disposable products to be discarded after having absorbed the respective liquid, significant amounts of petroleum based raw materials are needed and must be disposed of.

Accordingly, alternatives to the petroleum based raw materials have been sought. One such alternative raw material is protein from biomass, in particular plant protein or fish protein.

U.S. Pat. No. 5,847,089 discloses a protein hydrogel obtained by acylation of lysyl residues in a protein raw material derived from biomass. In addition to acylation, the protein raw material is subjected to crosslinking using a dialdehyde. In one example the acylation of soy protein isolate is performed at a protein concentration of 1-2% in water.

U.S. Pat. No. 9,643,157 discloses a hydrogel composition comprising crosslinked dextran and dextran sulphate.

In order to substitute conventional petroleum based absorbent materials with absorbent material based on protein from biomass, in particular plant based proteins, there arises a need for method capable of producing such absorbents having a high efficiency, using sufficiently cheap and easily obtained raw materials, and resulting in absorbent materials having competitive properties as regards absorption and retaining of liquids.

SUMMARY OF THE INVENTION

According to the present disclosure, there is provided an absorbent article for absorption of body fluids, comprising an absorbent member that comprises at least one plant protein based absorbent material obtainable a method comprising the steps of i. providing a mixture or suspension comprising a liquid and a plant protein, wherein said plant protein is insoluble in the liquid, ii. acylating said plant protein by adding an acylating agent thereto, and iii. obtaining said plant protein based absorbent material.

The absorbent article may be selected from disposable hygiene absorbent articles, such as diapers, incontinence pads, panty liners, tampons and bed protection sheets, and medical dressings, such as adhesive plasters and compresses.

Accordingly, the technology proposed herein is based on the realization that plant protein can be acylated to yield a plant protein based absorbent material suitable for use as absorbent material in an absorbent article, thereby reducing the dependency on petroleum based raw materials in the production of the absorbent articles. The technology is also based on the realization that the plant protein can be acylated to yield a plant protein based absorbent material even if the plant protein is not dissolved in a solution, but rather is provided insoluble in a liquid. As the plant protein is insoluble in the liquid it becomes easier to handle and separate. Thus the plant protein based absorbent material can be separated or recovered from the liquid or from the reaction mixture after the acylation efficiently for example using centrifugation, drying or filtration instead of first needing to be precipitated out. This saves time and makes the method more efficient. Additionally, any subsequent steps of cleaning or washing the acylated plant protein are also simplified as the plant protein is easier to handle and separate for example from a cleaning or rinsing liquid, e.g. using centrifugation.

This result is also surprising in that the acylating agent, which needs to be able to contact the plant protein, is evidently capable of reaching and affecting the insoluble plant protein in the liquid.

The method for acylating may be used with a wide variety of plant protein including plant proteins obtained from industrial product streams in which the plant protein is typically obtained in aggregated form, i.e. where the plant protein is so aggregated that it becomes insoluble in the liquid. This also provides for obtaining a plant protein based absorbent material while reducing or obviating the need for chemically crosslinking the plant protein when the plant protein based absorbent material is prepared and/or when it is used. This increases the efficiency of the method as a crosslinking step may require around 12 hours or more to perform, and crosslinking also decreases swelling capacity and can involve toxic chemicals. Aggregated plant protein can, inter alia, be obtained from industrial product streams, but the aggregation can also be effected deliberately. Aggregated plant protein is accordingly already sufficiently aggregated that mere acylation yields a sufficiently cohesive material capable of absorbing and retaining liquid. The method may however comprise a further step of chemically crosslinking the plant protein for further improving the strength and cohesion of the absorbent material when the absorbent material is used for absorbing liquids in which the plant protein is soluble.

Accordingly, the damage, i.e. aggregation, that is inflicted on a plant protein during industrial processing, to obtain a main product to which the protein is an industrial co-product stream, may according to the technology proposed herein, be utilized to make the process of producing the plant protein based absorbent material more efficient by obviating or reducing the need for chemically crosslinking the plant protein. This not only simplifies and decreases the cost of preparing a plant protein based absorbent material, it also provides a valuable use for aggregated plant protein obtained from industrial process streams, which protein otherwise, due to its content of other non-protein compounds or poor functionality, may not be used in food applications without further treatment.

In the context of the technology proposed herein the term preparing is to be understood as also encompassing the term producing.

Plant protein comprises protein obtained from plants. Plants include, inter alia, tubers (such as potato), cereals and other commercially and non-commercially grown plants.

The plant protein may be obtained from an industrial product stream, i.e. produced or obtained as a product of an industrial process. Examples of plant protein obtained from an industrial product stream include potato protein that is obtained as a product when potato tubers are processed for extracting starch, the starch being the main product of the industrial process.

The plant protein is provided in a mixture or suspension comprising a liquid and the plant protein. The liquid is preferably an aqueous liquid, such as water. For example, when potato protein is obtained as a by-product of starch extraction the potato protein may be provided as a suspension corresponding to the potato fruit juice, i.e. the liquid stream resulting after the extraction of the starch.

The liquid should preferably not inactivate the acylating agent or render it ineffective.

The plant protein may be rendered insoluble in the liquid by providing a liquid in which the plant protein is not soluble.

The plant protein may alternatively or additionally be rendered insoluble by being sufficiently aggregated so that it is insoluble in the liquid.

In step ii, the acylating agent may be added to the mixture or suspension. Alternatively, the liquid is removed prior to the addition of the acylating agent to the plant protein.

Preferably the plant protein is sufficiently aggregated so as to be insoluble in the liquid.

Preferably the plant protein is sufficiently aggregated so that it is insoluble in aqueous liquids, such as water. Water is a suitable liquid for use in the mixture or suspension.

One example of a plant protein suitable for use in the method is potato protein concentrate obtained as an industrial product stream from commercial starch extraction. Another example is wheat gluten.

The plant protein being insoluble in the liquid encompasses that the solubility of the plant protein is less than 1 g per liter, more preferably less than 0.1 g per liter of the liquid.

The plant protein may be obtained and provided in sufficiently aggregated form to be insoluble in the liquid. This is generally the case when the plant protein is obtained from an industrial product stream because industrial processes generally cause damage to plant protein so that it becomes sufficiently aggregated. Examples of such plant proteins are potato protein concentrate and wheat gluten protein.

Alternatively, the plant protein may be deliberately aggregated, for example by heat treatment including boiling or autoclaving a suspension of the plant protein, optionally with the addition of acid or base. The technology proposed herein then provides for preparing absorbent materials also from plant proteins which are not otherwise insoluble in a liquid by the simple step of aggregating them so they become insoluble.

During the acylation step the acylating agent may graft molecules charged carboxylic acid groups onto the plant protein molecules. These carboxylic acid groups, when in contact with a liquid, provide an electric repulsion of different parts of the protein molecules from each other, thus leading to swelling of the plant protein based absorbent material.

The acylating agent may be ethylenediaminetetraacetic dianhydride (ED). A preferred acylating agent is succinic anhydride (S), which, as shown in the examples, provides absorbent material with a high Fluid Swelling Capacity (FSC). Other acylating agents include ethylenediaminetetraacetic acid (E), 1,2,3,4-butanetetracarboxylic acid (B), and citric acid (C).

The amount of acylating agent used may for example be 20-30 wt. %, such as 25 wt. % relative to the amount of plant protein that is to be acylated. The acylation of the plant protein is preferably performed at a temperature of at least 20° C. (room temperature) but may be as high as 160° C.

The plant protein based absorbent material is to be understood as encompassing absorbent materials comprising plant protein, as well as absorbent materials consisting essentially of plant protein. Preferably the plant protein based absorbent material contains at least 70 wt. % plant protein, such as at least 80 wt. % plant protein, or more preferably at least 90 or at least 95, 99 or 100 wt. % plant protein.

The plant protein based absorbent material may advantageously be in the form of particles having a particle diameter of 0.01 to 5 mm, such as 0.05 to 1 mm, such as 0.05 to 0.5 mm. The desired particle size can be obtained by including a step of grinding or otherwise dividing the plant protein based absorbent material obtained in step (iii) into smaller particles.

Step (iii) of the method according to the first aspect of the technology proposed herein may further include a step of cleaning the absorbent material obtained after step ii. The absorbent material may, for example, be cleaned with water (by dispersing the material in water and centrifuging or filtering it). If desired the absorbent material may further be neutralized by adding an acid or base until a neutral pH is obtained, before obtaining the absorbent material in step (iii).

The liquid may be an aqueous liquid. Accordingly, the method may take as raw material a plant protein provided directly from an industrial product stream without requiring concentration, purification or isolation of the plant protein. This is advantageous in that it further decreases the cost, and increases the available sources of plant protein raw material, for the method. Alternatively, the plant protein can be obtained or provided in a mixture or suspension by mixing dry plant protein with a liquid, preferably an aqueous liquid such as water.

The plant protein should be insoluble in the liquid in the mixture or suspension. This allows the plant protein to be easily separated from the liquid after the acylation, for example using filtration or centrifugation as described further below.

Preferably, the plant protein is sufficiently aggregated to be insoluble in the liquid.

The pH of the mixture or suspension is preferably about 11, such as 10 to 12.

The pH may further be adjusted to at least 12 prior to step ii.

Generally, the content of plant protein in the mixture or suspension is from 2 wt. % to 90 wt. %, preferably from 2-75 wt. %, more preferably from 2-50 wt. % or 2-40 wt. %, with the remainder being made up preferably by the liquid alone or substantially only the liquid.

In some embodiments of the method the content of plant protein in the mixture or suspension is from 2 wt. % to 10 wt. %. Thus the method may use plant protein at lower concentrations thus making it easier to handle the mixture or suspension as it can be pumped or otherwise handled like a liquid.

In other embodiments of the method the content of plant protein in said mixture or suspension is from 10 wt. % to 40 wt. %. Surprisingly, as further evidenced by the example section, it is possible to acylate the plant protein at a starting plant protein content as high as 40 wt. %. This renders the method more efficient as it decreases required capacity for the reaction vessels used for the acylation. It further decreases the amount of liquid that must be removed from the absorbent product to obtain the final absorbent material reducing the energy needed.

Advantageously, in some embodiments of the method, step (iii) of obtaining the plant protein based absorbent material comprises centrifuging a reaction mixture obtained from step (ii) of acylating said plant protein. This is made possible by using plant protein that is insoluble in a solvent, e.g. the liquid, in which the acylation may be performed. Due to the insolubility of the protein there is no need for the conventional techniques of precipitating the protein based absorbent material using changes in pH to induce precipitation; rather the insoluble nature of the plant protein allows the use of centrifugation to separate it from the reaction mixture. It is further contemplated that other separation methods such as filtration could be used to separate the plant protein based absorbent material from the reaction mixture. The process is further simplified in that, whereas conventional techniques require re-suspending the reaction mixture and adjusting the pH, the centrifugation may be allowed to take place at the pH which was used during the reaction, i.e. during the acylation. This is especially useful when the content of plant protein in the mixture or suspension is from 2 wt. % to 10 wt. %. The rotation speed of the centrifuge may be 2500 to 4500 rpm (corresponding to Relative Centrifugal Force (RCF) values of about 1100 to 3400).

In alternative embodiments, wherein the content of plant protein in the mixture or suspension is from 10 wt. % to 40 wt. %, step (iii) of obtaining the plant protein based absorbent material may comprise dispersing the acylated plant protein in water after step (ii) and allowing it to dry. Thus at these higher concentrations mere drying i.e. allowing the liquid to evaporate, is sufficient to obtain the plant protein based absorbent.

The plant protein can be obtained using further methods. In some embodiments step (iii) of obtaining the plant protein based absorbent material comprises lyophilizing the plant protein after step (ii). This provides a plant protein based absorbent material having a porous structure capable of absorbing 9-10 g saline solution (0.9 wt. % saline, i.e. NaCl in water) per gram of the absorbent material after 9 seconds, and having a Centrifuge Retention Capacity (CRC) in said saline solution of 3 g/g at 1230 rpm (corresponding to 270 RCF) for 3 minutes. The absorbing capacity for blood, as tested using defibronated sheep blood, is comparable to conventional petroleum based absorbent materials at 4-8 g/g, and the maximum absorption occurs faster than for the conventional petroleum based absorbent material.

In other embodiments step (iii) of obtaining the plant protein based absorbent material comprises drying the plant protein after step (ii) at a minimum of 50° C. This provides solid particles absorbing 20-30 g/g of water and 9-10 g/g of saline solution (0.9 wt. %). The absorption was completed after 100 seconds. The CRC was 3-4 g/g for saline at the same RCF as above. The absorbing capacity for blood, as tested using defibronated sheep blood, is comparable to conventional petroleum based absorbent materials at 4-8 g/g at 30 minutes.

In still further embodiments step (iii) of obtaining the plant protein based absorbent material comprises oven-drying, drum-drying, spray-drying, freeze drying, fluid bed drying, microwave drying, microwave-vacuum drying, vacuum oven drying, shelf drying or flash-drying said plant protein after step (ii). This provides a particulate solid absorbent material.

The drying may be performed at a temperature of at least 30° C., such as at least 35, 40 or 50° C.

If desired the method may further comprise heat denaturing the plant protein at a minimum of 80° C., such as at least 90° C., for at least 30 minutes, prior to step (ii). The heat denaturing is preferably performed with the plant protein in a mixture or suspension comprising water and the plant protein, such as an aqueous dispersion. This further increases the cohesiveness of the absorbent material and increases physical strength and rigidity. This is because the heat denaturing opens up the protein molecules, thereby rendering them more reactive.

As stated above the method does not require any step of crosslinking. Thus, in preferred embodiments the method does not include any step of crosslinking the plant protein. This saves significant amounts of time, in some cases 12 hours. Further, by avoiding the need for crosslinking there is further no need to use toxic crosslinking chemicals which are added to the plant protein or that need to be handled or disposed of in the method.

In some embodiments the method however does comprise a step of crosslinking by adding a crosslinking agent to the plant protein. The crosslinking agent may be glutaraldehyde and/or genipin.

In some embodiments the method may further comprise the step of:

iv. adding genipin to the plant protein.

This is advantageous in that genipin, which is known as a non-toxic, bio-based, crosslinking agent, surprisingly, and in contrast to the expected effect of reducing the absorbing capacity of the absorbent material, instead increases the swelling capacity in the present method.

The amount of genipin added may be from 1 to 10 wt. % of genipin, such as 4 wt. % of genipin based on the weight of the acylated plant protein. The genipin is preferably added after the acylation step (ii), but may alternatively be added before. Genipin is preferably added at a temperature of at least 35° C., such as at least 40° C. The time needed for genipin to react with the plant protein may be at least 1 hour, such as 1-4 hour, such as 1-3 hours, such as 2 hours.

In preferred embodiments of the method the plant protein comprises potato protein. Potato protein, especially in the form known as Potato Protein Concentrate (PPC) is a readily available source of non-food grade plant protein and has shown itself to be suitable for the present method.

Other preferred plant proteins comprise wheat gluten protein and soy protein.

Whereas commercially obtained wheat gluten protein, as is the case with PPC, is aggregated when obtained, soy protein may be provided in aggregated state if needed by aggregating it as described above for being used in the method.

For wheat gluten the content of plant protein in the mixture or suspension is preferably at least 10 wt. %. However, lower concentrations can be used, preferably if genipin is also added to the plant protein.

Preferably, the industrial product stream is obtained from a starch extraction process, and the industrial product stream is obtained directly after a starch extraction step. Starch is produced in large quantities worldwide. By using plant protein from an industrial product stream obtained from a starch production process, the industrial product streams of the starch extraction can be better utilized. The method advantageously allows for using the protein containing industrial product stream directly after starch extraction.

A further aspect of the technology proposed herein concerns a plant protein based absorbent material obtained by the method according to the first aspect of the technology proposed herein.

The plant protein based absorbent material may preferably comprise potato protein, i.e. protein derived or obtained from potato. Alternatively, the plant protein based absorbent material may comprise wheat gluten protein. The plant protein based absorbent material may have a Free Swelling Capacity (FSC) according to any one of the below given values in table 1:

TABLE 1 characteristics of a plant protein based absorbent material

| Medium | FSC (gram media per gram of material) |
| --- | --- |
| Milli-Q ® water (ultrapure water of Type 1 according to ISO 3696) | At least 4 g/g at 300 seconds, more preferably at least 5 g/g at 300 seconds, or alternatively at least 8 g/g at 86400 seconds |
| 0.9 wt. % NaCl solution (saline) | At least 3 g/g at 10 seconds, or alternatively at least 3.75 g/g at 600 seconds |
| Defibronated Sheep blood | At least 5 g/g of defibronated sheep blood after 30 minutes |

The CRC (Centrifuge Retention Capacity) of the plant protein based absorbent material for 0.9 wt. % NaCl solution (saline) may be at least 2 g/g, such as at least 2.5 g/g.

In some cases the plant protein based absorbent material is substantially devoid of capillaries, whereas in other cases the plant protein based absorbent material may comprise capillaries.

A further aspect of the technology proposed herein concerns a plant protein based absorbent material comprising plant protein, wherein the plant protein is aggregated and acylated, and wherein the plant protein based absorbent material has a free swelling capacity (FSC) of at least 3 g of 0.9 wt. % NaCl solution (i.e. 0.9 wt. % NaCl in water) per gram absorbent material at 10 seconds.

The plant protein based absorbent material may further have a free swelling capacity (FSC) of at least 5 g defibronated sheep blood at 30 minutes, and/or a free swelling capacity (FSC) of at least 4 g ultrapure water of Type 1 according to ISO 3696 per gram absorbent material at 300 seconds.

BRIEF DESCRIPTION OF THE DRAWINGS

A more complete understanding of the above mentioned and other features and advantages of the technology proposed herein will be apparent from the following detailed description of preferred embodiments in conjunction with the appended drawings, wherein.

DETAILED DESCRIPTION

Figure 1A:
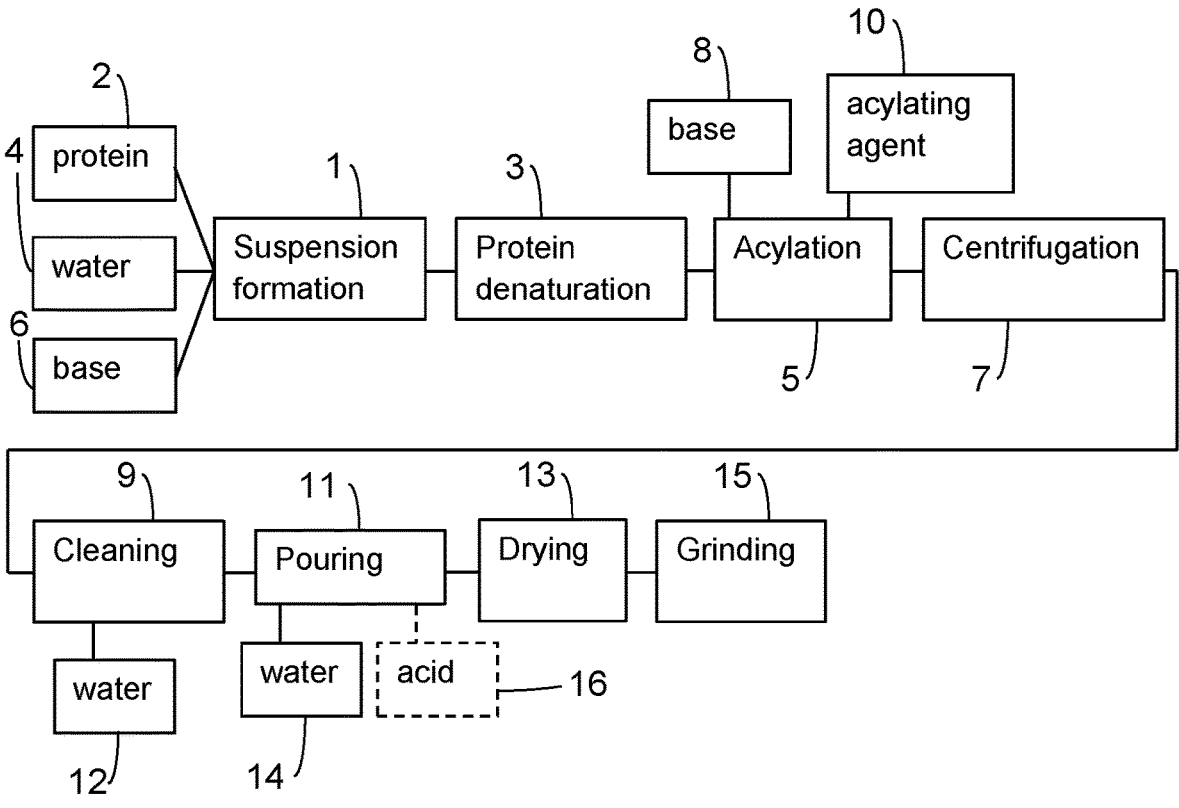
FIG. 1A shows a first embodiment of the method according to the first aspect of the technology proposed herein.

In the below description of the figures the same reference numerals are used to designate the same features throughout the figures. Further, where present, a "'" added to a reference numeral indicates that the feature is a variant of the feature designated with the corresponding reference numeral not carrying the "'"-sign.

The present disclosure relates to an absorbent article for absorption of body fluids comprising an absorbent member that comprises a plant protein based absorbent material as disclosed herein, as well as to the use of a plant protein based absorbent material, as disclosed herein, as an absorbent material in an absorbent member of an absorbent article for absorption of body fluids.

In the context of this disclosure, the term "body fluids" refers to urine, faeces, menstrual fluid and other vaginal discharges, blood, and wound exudates.

The absorbent article may be a disposable hygiene absorbent article in the shape of a bed protecting sheet or may be intended to be worn in the urogenital area of a user.

The disposable hygiene absorbent article may be a product intended to be worn and held in place against the body by an undergarment, such as a pad, for example an incontinence pad, a removable insert, or a sanitary napkin, or may be an absorbent product able to be worn and held against the body without external help from undergarment, such as an open-type diaper, a belt-type diaper or a pant-type diaper. The disposable hygiene absorbent article may also be a tampon.

The construction of hygiene absorbent articles as well as different materials for use in hygiene absorbent articles are well known in the art.

Figure 5:
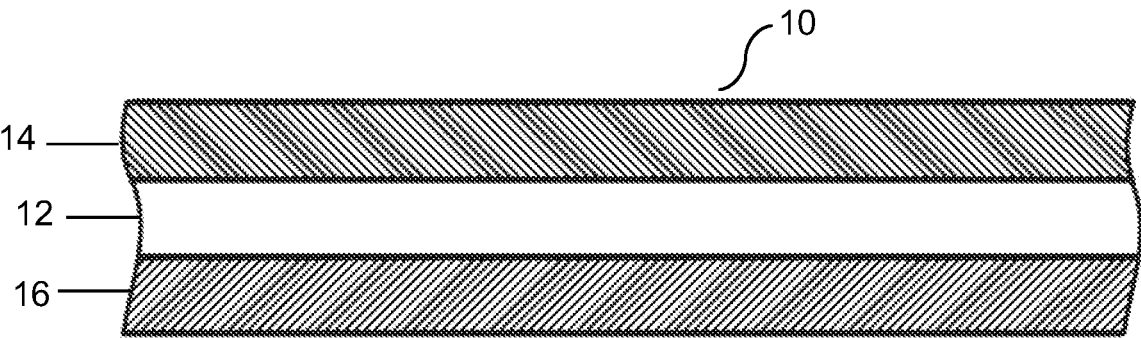
FIG. 5 is a schematic representation of an exemplary absorbent article with an absorbent member disposed between a first liquid permeable layer and a second layer.
Figure 6:
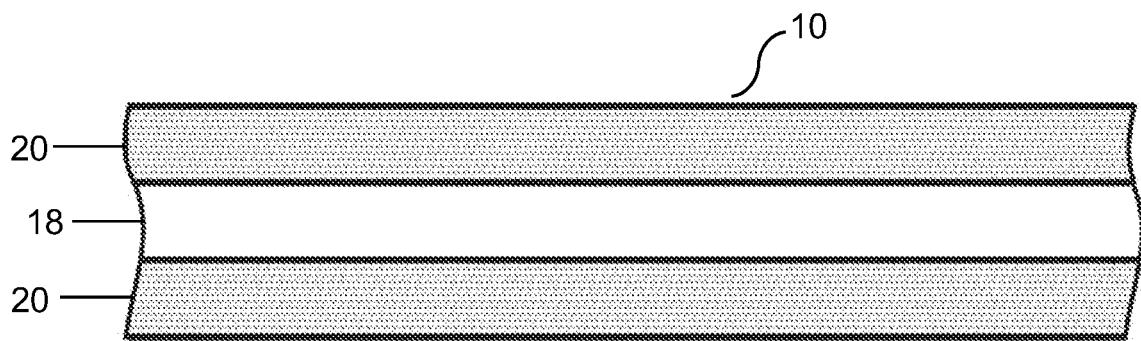
FIG. 6 is a schematic representation of an exemplary absorbent article with an absorbent member wrapped in a liquid permeable wrapping.

Referring to FIGS. 5 and 6, in a hygiene absorbent article 10, the absorbent member 12 may be disposed between a first, liquid permeable layer 14, conventionally referred to as "topsheet" and a second layer 16, conventionally referred to as "backsheet". This is the conventional construction of diapers, incontinence pads, sanitary napkins and bed protecting sheets. Alternatively, the absorbent member 18 may be wrapped in a liquid permeable wrapping material 20, such as in the case of tampons.

The topsheet may be of any material or combination of material suitable for use for this purpose, including but not limited to fibrous nonwovens, apertured plastic films and textile materials, allowing for body fluids or components thereof to be transported therethrough and absorbed in the absorbent member.

The backsheet may be of any material or combination of materials suitable for this purpose, including but not limited to non-wovens, plastic films and film-nonwoven laminates. The backsheet may be liquid impermeable to prevent leakage of body fluids therethrough. The backsheet may be vapour permeable, breathable, to allow vapour to pass therethrough.

Further components may be provided between the topsheet and the backsheet, such as an acquisition layer disposed between the topsheet and the absorbent member for improving the transport of liquids from the topsheet to the absorbent member.

The absorbent article may alternatively be a medical dressing, such as an adhesive plaster or compress, intended to be used in the treatment of wounds.

In medical dressings, the absorbent member may be disposed between a first liquid permeable layer and a second layer, or may be wrapped in a liquid permeable wrapping.

The construction of medical dressings, as well as different materials for use in medical dressings are well known in the art.

The plant protein based absorbent material may be the sole absorbent component of the absorbent member or may be combined with further absorbent components to form the absorbent member. Examples of such further absorbent components include, but are not limited to fibrous materials, such as cellulosic fibers, synthetic fibers, foam materials and further absorbent materials, such as based on cross-linked acrylic acid-based polymers.

The plant protein based absorbent material may constitute from 5 to 100% by weight of the total weight of absorbent material in the absorbent member.

The plant protein based absorbent material and methods for its manufacture will now be described in further detail.

FIG. 1A shows a first embodiment of the method according to the first aspect of the technology proposed herein. In this embodiment, termed "wet acylation" the plant protein is provided as a 2-10 wt. % suspension. The suspension is formed in a first step 1 by mixing plant protein 2 and water 4. Base, for example NaOH, is added to obtain a pH of about 11. Although this embodiment shows the step of forming the suspension 1 from dry aggregated plant protein from an industrial product stream, alternatively the aggregated plant protein in the product stream could already be in the form of a suspension, or a non-aggregated plant protein could be mixed with water to form a suspension where after the suspension was heated, and optionally treated with acid or base, to cause aggregation of the protein. In any case the pH of the suspension is preferably adjusted to about 11 using addition of base before acylation.

Following the step of forming the suspension 1 the protein may advantageously be heat denatured at a minimum of 90° C. for at least 30 minutes. After the heat denaturing the suspension is preferably cooled to room temperature, alternatively to 50° C. The pH may further be increased to 12 by the addition of base 8 in the first stage of the acylation 5. In the acylation step 5 an acylating agent 10 is added to the suspension. The acylating agent, in this case ED, is preferably added gradually during a time interval, such as 1-45 minutes, for example 30 minutes, until 25 wt. % acylating agent, related to the amount of plant protein in the suspension, is reached. Acylation is then allowed to carry on for 1 to 3 hours, such as 1.5 hours, while further base 8 is added as needed to keep the pH at at least 11, preferably at 12.

Due to the aggregation of the plant protein, the acylated protein is insoluble and advantageously separated from the suspending water by centrifugation 7 at, for example, 2500 RPM or about 1100 RCF.

The thus obtained plant protein based absorbent material is then advantageously cleaned by removal of the supernatant and adding clean water 12. The water 12 should preferably have a pH of about 11 through the addition of a base. Following the resuspension of the absorbent material in the clean water 12 the suspension is once more centrifuged to separate the plant protein based absorbent material from the cleaning water. The plant protein based absorbent material is then, after removing the cleaning water and resuspending the material in further water 14, poured on a flat surface or in a mould. Acid 16 may optionally be added before pouring to neutralize the pH to about 7. Finally the poured plant protein based absorbent material is allowed to dry, for example at room temperature or higher, such as for example at 30° C., 35° C. up to about 50° C. or even 55° C. The drying time obviously varies with the amount of plant protein based absorbent material that is to be dried and its water content, but may generally be in the range of 2-24 h such as 5 hours. The dry plant protein based absorbent material is then advantageously ground 15 into granulate or powder.

Figure 1B:
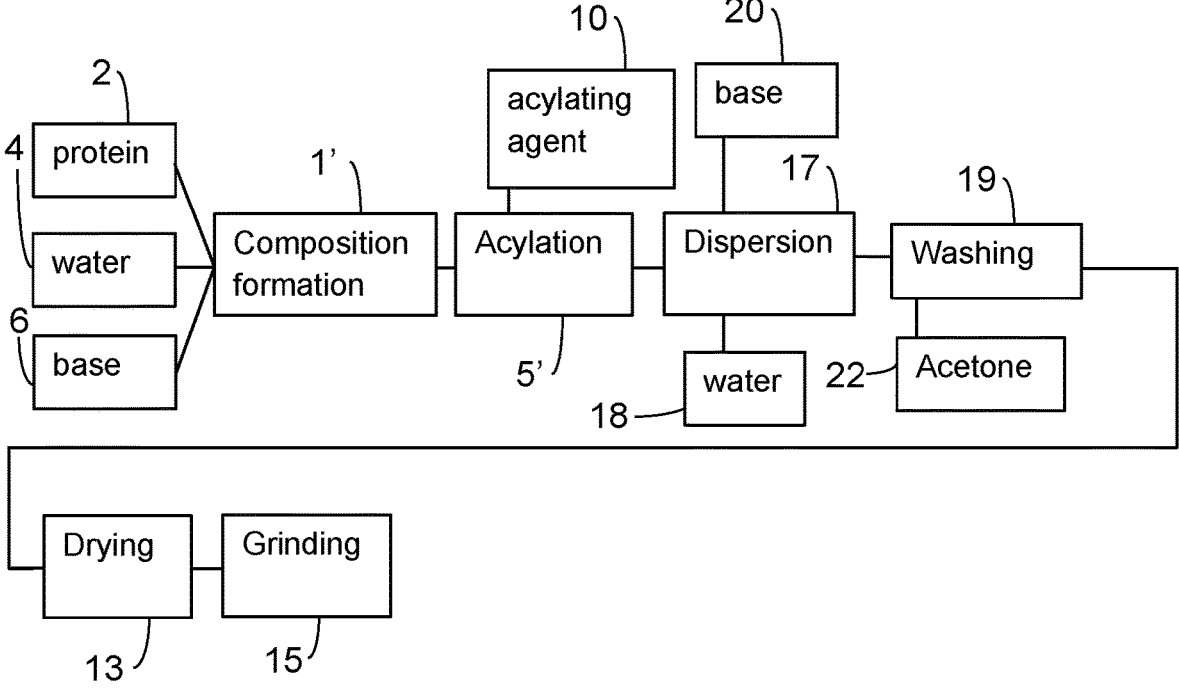
FIG. 1B shows a second embodiment of the method according to the first aspect of the technology proposed herein.

FIG. 1B shows a second embodiment of the method according to the first aspect of the technology proposed herein. In this embodiment, termed "drier acylation" the plant protein is provided as a 40 wt. % suspension forming a mixture or dough.

The mixture is formed in a first step 1' by mixing plant protein 2 and water 4 into a dough. Base, for example 1M NaOH, is added to obtain a pH of about 11.

Although the second embodiment shown in FIG. 1B does not utilize a step of heat denaturing the plant protein, such a step may nevertheless be included in this second embodiment. If the plant protein 2 is not already insoluble in the suspending liquid, for example by being sufficiently aggregated, it may be heated, and optionally treated with acid or base, to cause it to aggregate.

After forming the mixture a modified acylating step 5' ensues in which the mixture is placed in a reaction vessel connected to a dean-stark apparatus for condensing any solvent, in this case condensing water released from the water that was mixed with the plant protein initially and water from the ester formation of the condensation reaction. An acylating agent 10 is added to the suspension. The acylating agent, in this case ED is added until reaching a mass ratio of 0.5:1 (protein:acylating agent). The reactor vessel is heated at a rate of about 1° C./min from ca. 70° C. to 100° C. while stirring (ca. 30 min) to evaporate water from the mixture. Thereafter the temperature is raised at 10° C./min to the acylation temperature and kept constant for 1 to 3 hours, such as 1.5 hours.

Upon conclusion of the acylation, the mixture, now having the consistency of a paste, was dispersed 17 in water 18 while the pH of the dispersion was raised to neutral by the addition of base 20, such as NaOH. The dispersed absorbent material was filtered and washed 19 using acetone 22. As an alternative to acetone, ethanol or water at pH 11 can be used for the washing step 19. Finally, the plant protein based absorbent material is allowed to dry, for example at about 50° C. The drying time obviously varies with the amount of plant protein based absorbent material that is to be dried and its water content, but may generally be in the range of 2-24 h such as 5 hours. The dry plant protein based absorbent material is then advantageously ground 15 into granulate or powder.

Although FIGS. 1A and 1B show embodiments of the method using PPC as the plant protein, other plant proteins can be used in the method. One example is wheat gluten (WG). When WG is used as the plant protein, the method is carried out generally as shown in FIG. 1A, however the suspension obtained in the suspension formation step 1 should preferably have a content of wheat gluten protein of at least 5 wt. %, preferably at least 10 wt. %. Further, optionally, the pH of the of the acylated wheat gluten protein may be adjusted to 2-3 with HCl (1M) to flocculate the protein before the centrifugation 7. In this case the cleaning 9 is carried out using water at pH 2-3. Before pouring 11 the pH of the suspension is adjusted (if necessary) to neutral or alkaline (ca. 11) with base instead of acid 16, and the suspension is poured on a flat surface and dried as described above.

Further, genipin may be added before or after the acylation step 5.

EXAMPLES

Example 1: Acylation of Potato Protein Concentrate from Concentrated Water Suspension 1.1. Background Potato protein concentrate (PPC) is an inexpensive by-product from the agricultural industry of starch extraction. Due to the content of non-protein compounds, such as glycoalkaloids, from the industrial process, the protein is not used in food applications. The protein is in particular aggregated due to the industrial treatment.

The purpose of this example is to investigate the possibility of a fully PPC based absorbent material that displays high swelling properties in water, blood and saline solutions.

1.2 Materials and Methods 1.2.1 Materials

Commercial potato protein concentrate (PPC) was provided by Lyckeby Starch AB, Sweden, with protein content corresponding to 82±2 (Dumas method, Flash 2000 N C Analyzer, Thermo Scientific, USA, Nx6.25), and a moisture content of 8.1±0.4%. The PPC powder was used as received.

As for the acylating agents, ethylenediaminetetraacetic dianhydride 98% (ED), ethylenediaminetetraacetic acid ≥99% (E), succinic anhydride ≥99% (S), 1,2,3,4-butanetetracarboxylic acid (B) 99%, and citric acid ≥99.5% (C), were all purchased from Sigma-Aldrich.

1.2.2 Methods

The PPC powder was mixed in a beaker with MilliQ quality water (MQw) until a homogenous protein-rich dough or suspension was formed with a ca. 40 wt. % PPC concentration. Thereafter, 1M NaOH solution was added dropwise to the dough until reaching a pH of 11, i.e. for unfolding the PPC. The content from the beaker was then transferred to a reaction chamber, connected to a dean-stark apparatus, as well as a mixer. The reactor was placed in an oil bath preheated to 70° C.

The PPC was acylated using the five different acylating agents, S, B, ED, C, E, which were added through an opening of the reactor. The mass ratio for each acetylation agent was kept constant and 0.5:1 ratio for Protein:acetylation agent. Thereafter, the reactor was covered with an aluminium foil to prevent condensation on the interior above the oil bath. The temperature of the reactor was set to increase at a rate of ca. 1° C./min from ca. 70° C. to 100° C. to evaporate the residual water contained in the dough. At the time when a paste-like fluid had formed (after ca. 30 minutes) the temperature was increased at 10° C./min from 100° C. to the selected targeted temperatures of 120, 140 and 160° C.

As the targeted temperatures were reached, the duration of the reactions was 1.5 h. The approximate time for the evaporation of most of the contained water in the dough was ca. 45 min, out of the 1.5 h reaction time (indicated by absence of condensation in the condensation unit). The reactor was then opened and the warm paste was transferred to a beaker containing 200 ml±1 ml MQw. The suspension was thoroughly mixed for removal of the unreacted sodium salts of the acylating agent, followed by a neutralization step. The pH of all the suspensions before neutralization (to pH 7) was ca. 2-3.

The suspensions were filtered using a filter paper N3 and finally rinsed with acetone (also ethanol and water can be used for rinsing). Due to the increased solubility in some of the treated PPC samples, some suspensions were centrifuged at 1.200 rpm (260 RCF) at the reaction pH (ca. 2-3) before the neutralization and filtration process. These samples are marked with an * in table 2 below. After the centrifugation, the supernatant was replaced by fresh water, and the mixture was re-dispersed and neutralized. All the clean and neutralized PPC samples were dried overnight at 50° C. An identically treated PPC sample was produced as reference, i.e. without the addition of any acylating agent (named PPC11). Table 2 summarizes the material protocols tested.

TABLE 2

| materials protocols | | |
| --- | --- | --- |
| NAME | ACYLATING AGENT | TEMPERATRE (° C.) |
| PPC11 | None | 120 |
| PPC/S/120 | Succininc | 120 |
| PPC/S/140 | anhydride | 140 |
| PPC/S/160* | | 160 |
| PPC/B/120 | Butanetetracarboxylic | 120 |
| PPC/B/140* | acid | 140 |
| PPC/ED/120 | Ethylenediaminetetraacetic Dianhydride | 120 |
| PPC/C/120 | Citric | 120 |
| PPC/C/140 | acid | 140 |
| PPC/E/120 | Ethylenediaminetetraacetic acid | 120 |

1.3. Analyses

Water and saline Free Swelling Capacity (FSC) The free swelling capacity (FSC) of the samples was determined using the "tea-bag" test, according to the standardized procedure of NWSP 240.0.R2.

Three bags filled with 100-200 mg of material per sample being tested. A nonwoven fabric 40×60 mm$^2$, 300-450 mesh (openings of 25-50 μm) with heat-sealed edges was used as the bag, and the filled bags were stored in desiccator for a minimum of 12 h prior the test. All bags were hooked to a holding rod and simultaneously immersed in a beaker containing MQw. After the immersion, the bags were placed on a paper towel for 10 sec for removal of excess of water, and the weight of the bags were recorded after immersion for 60, 300, 1200, 3600 and 86400 s (W$_i$). Three empty dry (W$_{db}$)

bags were handled identically to obtain a correction factor ($W_{blank}$), and then soaked in MQw for 86400 s ($W_{wb}$). The correction factor was obtained as an average of the three replicates. The swelling was calculated according to:

$$W_{blank} = W_{wb}/W_{db}$$

$$FSC = ((W_i - (W_b * W_{blank})) - (W_d))/W_d$$

Centrifuge Retention Capacity (CRC)

Approximately 100-200 mg of the powder samples were heat-sealed in 40×60 mm² bags of the nonwoven fabric as in FSC. The bags were immersed in 0.9% NaCl solution for 30 min. Thereafter, the bags were centrifuged at 1230 rpm (270 RCF) on top of glass beads during 3 min and the weight of the bags were recorded ($W_c$). The centrifuge retention capacity of the samples was determined according to:

$$CRC = ((W_c - (W_e * W_{blank}) - W_d))/W_d$$

Equally prepared blanks based on empty bags were tested. Three samples were measured and the average is reported.
Blood Absorption Blood absorption was determined following the same procedure as for the free swelling capacity determination. Defibronated sheep blood was used as the test liquid. The swelling capacity of 100-200 mg of material after 30 min of swelling was determined in duplicates. A commercial SAP was used as a reference material.

Size exclusion liquid chromatography SE-HPLC The protein solubility was evaluated by means of size-exclusion high-performance liquid chromatography (SE-HPLC) in Waters HPLC equipment, using a BIOSEP SEC-4000 Phenomenex column using a mobile phase of 50:50 water: acetonitrile with 0.1% trifloroacetic acid flowing at 0.2 ml/min. Briefly, 0.5 wt. % sodium dodecyl sulfate (SDS) 0.05M $NaH_2PO_4$ (pH 6.9) was used as extraction solvent in combination with multiple ultra-sonication steps. The first extraction (Ext. 1) was obtained from the supernatant (SN) of a centrifuged dispersion of 16 mg of the ground material in an SDS-phosphate solution. In the second extraction (Ext. 2), the centrifuged pellet from Ext. 1 was re-suspended in a new SDS-phosphate solution followed by a 30 s ultra-sonication. The third extraction (Ext. 3) of the centrifuged pellet from Ext.2 was performed with fresh SDS-phosphate solution and repeated ultra-sonication (30+60+60 s). Three replicates were used. The amount of extracted protein was normalized with that of the raw PPC (total extraction from the three extraction steps). The area of the 210 nm absorption chromatogram was arbitrarily divided into polymeric proteins (PP) and monomeric proteins (MP) at 15 minutes of elution.

1.4 Results

Figure 2A:
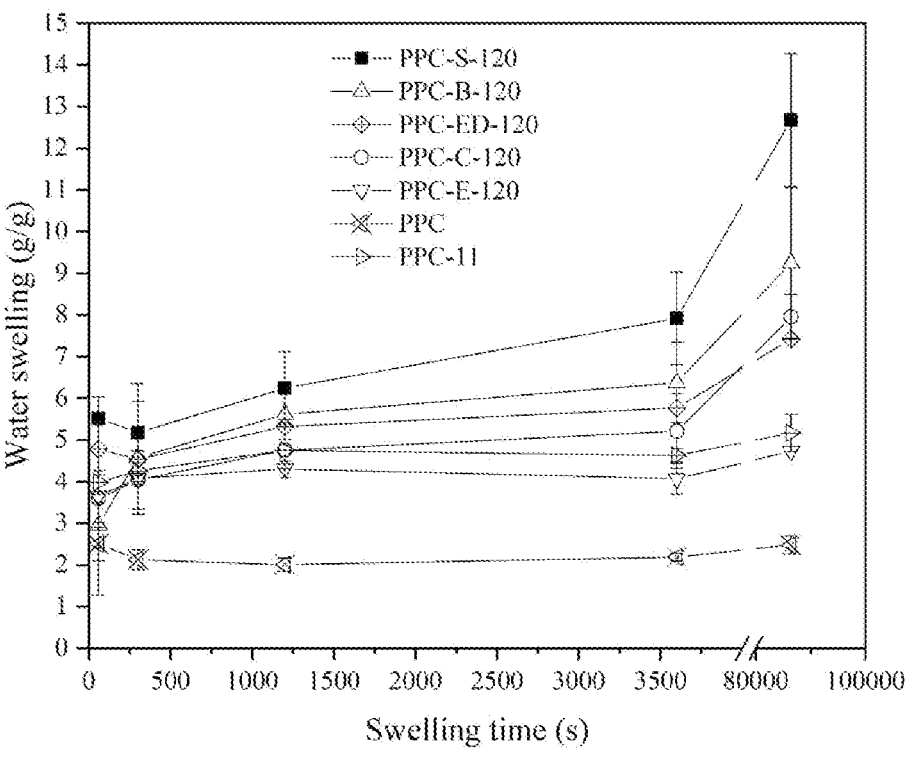
FIG. 2A shows FSC results obtained in example 1 for different acylating agents.

FIG. 2 shows the water swelling results obtained for the five acylating agents used at the reaction temperature of 120° C. It was observed that a rapid swelling in water occurred within the first 60 s of FSC, being the highest for PPC/S/120 and lowest for PPC, with 6 g/g and 2 g/g, respectively (see FIG. 2A). At longer times, PPC/S/120 still showed the highest FSC reaching a water swelling of ca. 14 g/g (equivalent to ca. 1500% weight increase) after 24 h. S was followed by B, ED, C and E in terms of the swelling uptake. The swelling of the high pH-treated PPC (PPC11) doubled the as received PPC. The pH treatment aids protein unfolding and disaggregation as well as giving some osmotic contribution to the material swelling. This fact is an indication of the important role that the protein structure plays when it comes to chemical modification of the protein towards water absorbent properties.

Figure 2B:
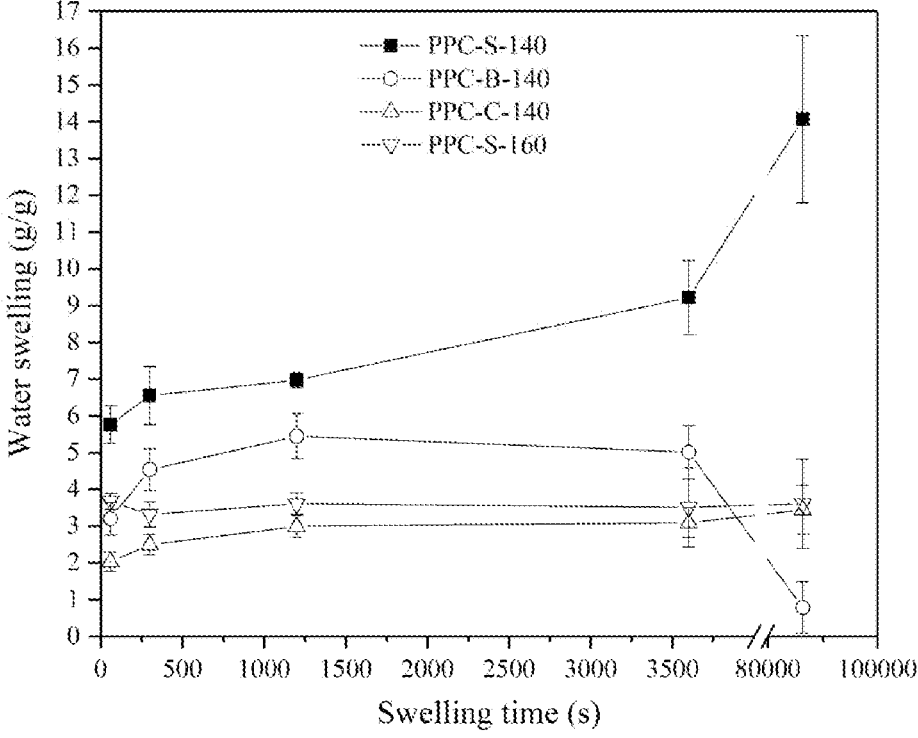
FIG. 2B shows FSC results obtained in example 1 for different acylating temperatures.

The acylation with succinic anhydride (S) showed an increase in the water swelling by ca. 14% when the reaction temperature was increased to 140° C. (see FIG. 2B). On the contrary, an unexpected material loss was observed for PPC/B/140 (not observed in PPC/B/120) after 30 min of swelling, as seen in FIG. 2B. Further SE-HPLC analysis showed that this set of conditions resulted in the sample with the highest monomeric fraction among the investigated conditions, indicating de-polymerization of the originally aggregated industrial potato protein when treated with B under these conditions.

Figure 2C:
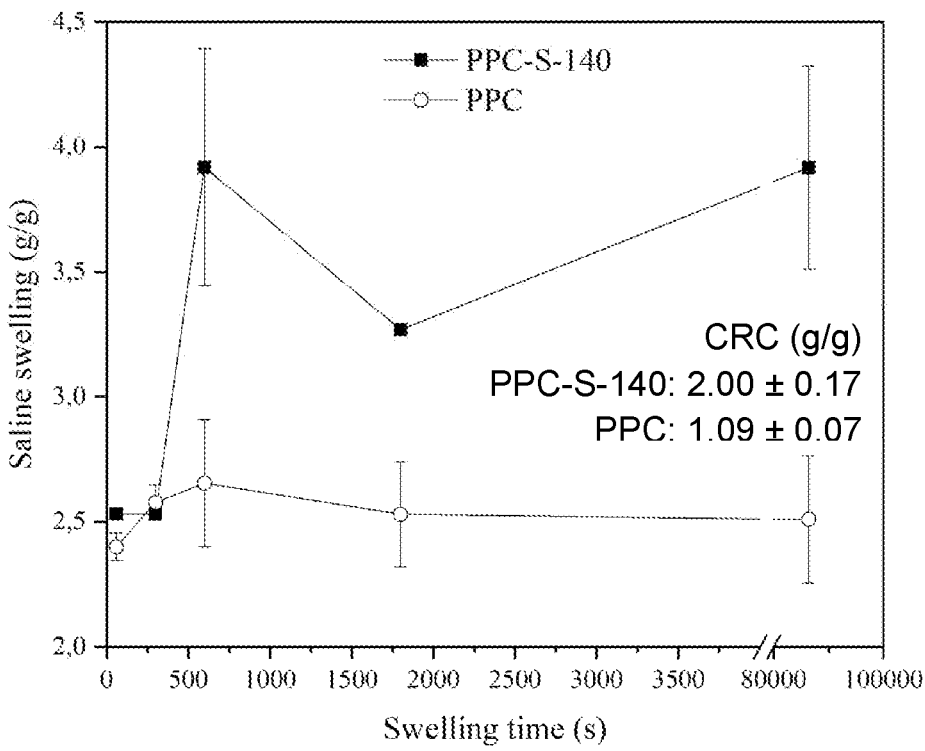
FIG. 2C shows the FSC results obtained in example 1 versus that obtained for untreated PPC.

The FSC in 0.9 wt. % NaCl solution showed that PPC/S/140 reached its maximum swelling already after 10 min of swelling with 4 g/g absorption (in contrast to the 2.5 g/g absorption for PPC, see FIG. 2C). The decrease in swelling capacity of the material in saline solution is due to the osmotic pressure and charge screening effects that are affected when mobile ions are present in the liquid. Still, the behaviour and maximum swelling capacity in both water and saline solution of the acylated materials resembles the standard swelling ranges for SAPs. Additionally, a CRC of approximately 2 g/g was obtained for the aforementioned material, double of what is obtained for the reference PPC. The CRC value for PPC/S/140 (see data in FIG. 2C) also indicates that at least 50% of the saline solution reported by FSC is held within the bio-based absorbent.

The increase in both saline swelling and CRC compared to the reference sample demonstrated an increase in the ionic strength and water affinity, respectively, of the bio-based materials herein described. An additional 0.9 wt. % NaCl FSC and corresponding CRC test made on a commercial SAP revealed that also 50% of the saline solution is held within the synthetic polymer. Noteworthy is that the functionalization process herein applied does not reach the molar amount of carboxylic acid groups present in fossil-based SAPs (e.g. polyacrylic acid) where SAPs rely much more on their high content of charges on the polymer to generate high saline swelling values (above 40 g/g). Nevertheless, the materials made here were still able to hold the saline liquid within the acylated PPC (e.g. PPC/S/140) up to superabsorbent ratios. These results show the potential of this chemically modified potato protein industrial product stream to be considered as a sustainable and biodegradable absorbent material, utilizing inexpensive acylating agents and readily available and non-food grade PPC starting material. The suggested process is also environmentally friendly with potential industrial scalability.

Additional defibronated sheep blood absorption tests showed that PPC/S/120 was able to swell 5.35±0.23 g/g of blood after 30 min, which is approximately half of the blood absorption obtained for commercial SAP, this being 10.39±3.05 g/g. The defibronated sheep blood absorption after 30 min for the as received PPC powder was 3.22±0.01 g/g. These results indicate that these materials have the potential to perform in other daily care applications where SAP particulates are used, e.g. sanitary pads and biomedical applications.

The SE-HPLC results obtained after the 3 step protein extraction procedure show a clear increase in the MP fraction for the samples PPC/B 140, PPC/C/140 and PPC/S/160, see table 3 below:

TABLE 3

| | | | SE-HPLC results | | |
|---|---|---|---|---|---|
| Sample | Total PP % | Total MP % | Ext1% of total extracted for PPC | Ext2% of total extracted for PPC | Ext3% of total extracted for PPC |
| PPC | 45 | 55 | 25 | 20 | 55 |
| PPC/S/120 | 63 | 37 | 120 | 120 | 100 |
| PPC/S/140 | 53 | 47 | 220 | 150 | 20 |
| PPC/S/160* | 15 | 85 | 220 | 15 | 0 |
| PPC/B/120 | 63 | 37 | 60 | 145 | 130 |
| PPC/B/140* | 10 | 90 | 245 | 15 | 0 |
| PPC/ED/120 | 67 | 33 | 25 | 30 | 100 |
| PPC/C/120 | 65 | 35 | 60 | 125 | 180 |
| PPC/C/140 | 20 | 80 | 245 | 15 | 0 |
| PPC/E/120 | 66 | 34 | 35 | 50 | 185 |

This indicates that the protein undergoes severe hydrolysis due to the reaction conditions when using B and C at temperatures above 120° C., and S above 140° C. These results corresponded to the high material loss observed for the aforementioned samples and the negative effect in the swelling results, as seen in FIG. 2B. Nonetheless, the balance between monomeric and polymeric fractions for PPC/SA 140 was sufficient to improve the swelling properties while keeping the protein network together. On the contrary, the increase on the polymeric fraction above 50% for the rest of the samples could be the reason for limited uptake, i.e. the aggregation/polymerization of the protein decreases the swelling of the material due to restriction of network expansion. All the samples that showed an increase in the FSC in water also showed an increase in the total relative amount of extractable proteins (using the unmodified PPC extraction as reference), indicating an increase in the protein solubility.

Without wishing to be bound by theory the increase in the total protein extraction observed by HPLC for all the treated samples could stem from changes in the protein molecular structure, i.e. unfolding, chemical structure changes, molecular weight variations, etc., which affects the light absorption of the samples. This could influence the total extraction as the HPLC technique depends on the light absorption properties of the proteins. The total protein extracted in the 2nd and 3rd extraction steps (30 s and 30+60+60 s, respectively) was higher for those samples that showed less FSC, i.e. PPC/B 120, PPC/ED 120, PPC/E 120, and PPC/C 120.

The SE-HPLC results further show the different aggregation states between the commercially obtained (aggregated) PPC and the mildly extracted PPC produced through ammonium sulphate salting out performed on potato juice. The mildly extracted potato protein (PPCm) (not aggregated and water soluble) had a SDS extraction (Ext. 1), of 75%, SDS+Sonication 30 s (Ext. 2) of 20% and SDS+Sonication 30+60+60 s (Ext. 3) of 5%. In contrast commercially obtained PPC has Ext.1 of 25%, Ext. 2 of 20% and Ext. 3 of 55%. This clearly indicates the high amount of energy that has to be put into the system to solubilize the protein fractions of the commercially obtained PPC.

Furthermore, for the PPCm the monomer fraction is 70% of the total extractable protein content, whereas for the PPC the monomer fraction is 50% of the total extractable protein, which shows that PPC is aggregated in relation to PPCm.

Example 2: Acylation of Potato Protein Concentrate from Dilute Water Suspension 2.1 Background The purpose of this example was to investigate the possibility of a potato protein based absorbent material obtained using acylation at lower protein concentrations e.g. 2 wt. % "wet acylation". A further purpose of this example was to evaluate the effect of adding a crosslinking agent to the material.

2.2 Materials and Methods 2.2.1 Materials

Commercial Potato Protein Concentrate (PPC) was as in Example 1

In addition mildly extracted PPC (PPCm) was obtained from potato tubers by extracting the protein with ammonium sulphate precipitation.

Ethylenediaminetetraacetic dianhydride 98% (ED) and Glutaraldehyde (GA, 50% solution) were purchased from Sigma-Aldrich.

2.2.1 Methods

PPC was dispersed in a MQw pH 11 solution until a concentration of 2 wt. % protein was obtained. While adding the protein to the solution, the pH was continuously adjusted to 11 by adding 1M NaOH. Once the protein was homogenously dispersed (ca. 5 min), the dispersion was heated to 90° C. for 30 min to promote denaturation of the protein. Thereafter, the beaker was cooled down to room temperature and the pH adjusted to 12. Incremental amounts of ED were added to the beaker corresponding to 25 wt. % ED based on the protein content. The reaction was continued for 1.5 h with the pH maintained at 12 by adding 1M NaOH. The acylated protein was centrifuged at 4.500 rpm (3400 RCF) for 5 min, washed with fresh MQw at pH 11 and re-dispersed with a vortexer for 15 min.

At this point a crosslinking agent was optionally added:
a) 1 wt. % of glutaraldehyde added dropwise (based on the total amount of protein)

The glutaraldehyde treated suspension was left to cure for ca. 12 h at a temperature above room temperature (25-45° C.). Both dispersions were poured into petri dishes and dried in a forced air oven overnight, 40° C. for the glutaraldehyde treated acylated PPC, 55° C. if no glutaraldehyde was added. The dried films were ground to obtain particles.

2.3 Analyses

Analyses of the material were performed as described in example 1.

2.4 Results

The mildly extracted PPC (PPCm), when acylated, did not yield a material for which a FSC curve could be obtained as the material was lost from the test bags. It was found that PPCm was highly soluble in contrast to the PPC which was aggregated with about 40% more strongly bonded β-sheets compared to PPCm (from FT-IR). Thus the state of the PPC gives it a sufficiently crosslinked network to be stable on immersion after acylation, and there is no need for further crosslinking.

Figure 3A:
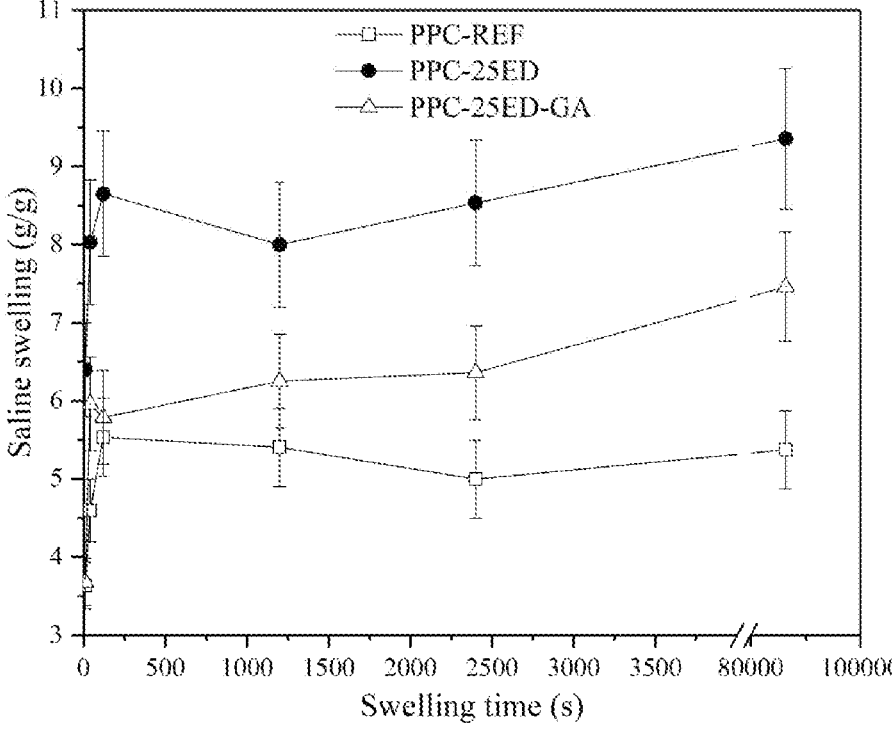
FIG. 3A shows FSC results obtained in example 2 with and without crosslinking.

FIG. 3A shows the FSC for saline solution absorption of the acylated PPC with and without crosslinking by glutaraldehyde (GA) as well as a reference PPC sample which is neither acylated nor crosslinked. It was found that crosslinking impairs the FSC in comparison to acylation only, thus indicating that the commercially obtained, aggregated PPC can be used without chemical crosslinking.

Figure 3B:
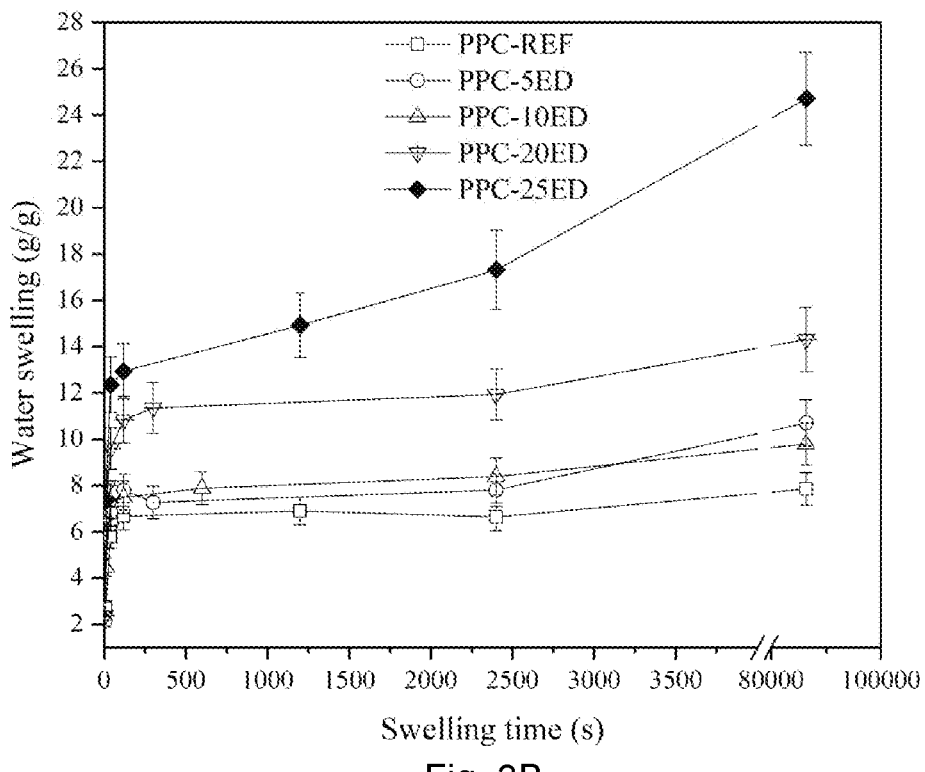
FIG. 3B shows FSC results obtained in example 2 using different amounts of acylating agent.

FIG. 3B shows the FSC for water for the acylated PPC at different proportions of acylating agent to PPC. A higher proportion of acylating agent (25 wt. %) provides a higher FSC.

Figure 3C:
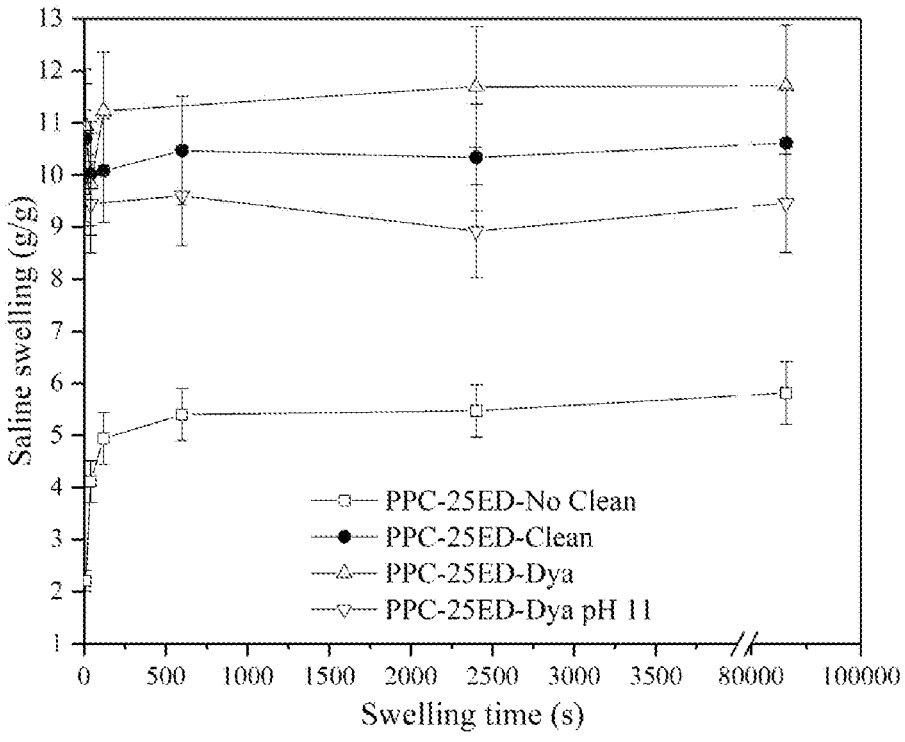
FIG. 3C shows FSC results obtained in example 2 depending on the type of cleaning/washing that is performed after the acylating step.

FIG. 3C shows the FSC for saline solution for the acylated PPC (25 wt. % acylating agent) obtained after different steps of cleaning/washing. The cleaning/washing steps remove unreacted sodium salts of the acylating agents. This can be performed at room temperature. Here "No Clean" refers to no cleaning after the centrifugation, "Clean" refers to resuspension of the absorbent material after centrifugation, and "Dya" refers to cleaning by dialysis (3000 Da molecular weight cut off) after pH adjustment to neutral, and "Dya pH 11" refers to dialysis without pH adjustment.

As seen in FIG. 3C, a cleaning step is advantageous in increasing the FSC of the absorbent material, however there is less need to adjust the pH as all "Clean", "Dyal" and "Dya pH 11" yield similar FSC, a neutral pH however being preferred for daily-care application as products which may come into contact with skin should not have high pH.

SE-HPLC was performed in order to determine if the water acylation protocol was severely damaging the PPC protein. The results are shown in table 4 below:

The characterization was carried out on each reaction step the protein is subjected to in achieving the final acylated product. Mildly extracted protein (PPCm) was used as the reference material. The protein extractability increased through every reaction step, an indication of increased protein solubility. PPCm is a highly soluble protein before treatment, contrary to commercially obtained PPC which is highly-aggregated, with ca. 40% more strongly bonded β-sheets than PPCm. The high aggregation state of the commercial PPC gives a sufficiently crosslinked network for low solubility even before functionalization has taken place. Consequently, there is no need for the addition of crosslinking additives in this system after the acylation of the PPC. Hence, the potential of this protein as a candidate in bio-based superabsorbent applications manufactured with less toxic substances is shown.

The HPLC results showed that acylation of commercial PPC led to a decrease in extractability after the acylation. Therefore, an increase in the crosslinked state of the protein structure, after the acylation, was obtained. This can be proposed as an effect that influences the functionalization behaviour, promoting an increased crosslink formation and thus less water absorption potential due to reduced network expansion.

Example 3: Acylation of Wheat Gluten Protein from Dilute Water Suspension 3.1 Background The purpose of this example is to demonstrate the possibility for a wheat gluten protein based absorbent material obtained using acylation at concentrations of 10 wt. % through "wet acylation".

3.2 Materials and Methods 3.2.1 Materials

Commercial wheat gluten concentrate (WG) was obtained from Lantmännen Reppe AB, Sweden. The reported protein content is 86.3±0.3 (Dumas method, NMKL 6:2003, USA, Nx6.25), the moisture content is 6.6±0.6%, fat and ash are 0.9±0.1 and 0.8±0.1% (2009/152/EU mod and NMKL 173), respectively.

For comparative purposes and to eliminate the influence of the commercial WG on the reactions, mildly extracted gluten was also used (WGm). The extraction of WGm was carried out by wrapping 20-30 g of wheat flour in a piece of

TABLE 4

| | | | SE-HPLC results | | |
|---|---|---|---|---|---|
| Sample | Total PP % | Total MP % | Ext1% of total extracted for PPCm | Ext2% of total extracted for PPCm | Ext3% of total extracted for PPCm |
| PPCm | 27 | 73 | 73 | 23 | 4 |
| PPCm/pH12 | 38 | 62 | 71 | 13 | 2 |
| PPCm/afterT | 56 | 44 | 84 | 5 | 1 |
| Funct/PPCm | 48 | 52 | 95 | 2 | 0 |
| Funct/PPCm/GA | 68 | 32 | 89 | 6 | 1 |
| PPC | 53 | 46 | 12 | 9 | 23 |
| PPC/pH12 | 51 | 47 | 12 | 9 | 23 |
| PPC/afterT | 44 | 58 | 17 | 6 | 17 |
| Funct/PPC | 30 | 65 | 19 | 4 | 10 |
| Clean/PPC | 53 | 27 | 2 | 4 | 22 |
| Funct/PPC/GA | 48 | 50 | 0.5 | 0.4 | 1 |
| SN/after cleaning | 2 | 98 | 39 | 1 | 0 | fine cloth and thoroughly washing it with running water thus removing the starch. The gluten rich fraction was frozen at −80° C. and lyophilized for 72 h. The WGm protein content (Dumas method, Thermo Scientific Flash 2000) was 85.5±0.6%.

Ethylenediaminetetraacetic dianhydride 98% (ED) and Glutaraldehyde (GA, 50% solution) was purchased from Sigma-Aldrich. Genipin 98% (G) was purchased from Zhi Xin Biotech company.

3.2.1 Methods

The acylation of the wheat gluten protein was generally conducted as in example 2, with the main difference that the concentration of the protein was 2 wt. % and 10 wt. % in alternative samples. The pH of the suspension was adjusted to 11. Heat denaturing was performed at 90° C. Acylation was performed at pH 12 using the acylating agent ED at a final concentration of 25 wt. % relative to the protein content. Afterwards, the pH was lowered to 3.5 to flocculate the protein and remove unreacted ED-salts. The suspension was centrifuged at 2500 rpm and the supernatant discarded, the pellet was resuspended in water and centrifuged, then resuspended and centrifuged once more. The pH was adjusted to neutral or pH 11, and the suspension was poured on a glass petri-dish, dried overnight in a forced air oven at 50° C. and ground to particles. Reference samples were similarly treated except for the acylation.

A further experiment was done to study the effect of adding genipin.

In a first experiment 4 wt. % of genipin, according to the amount of WG, was added to a dispersion of 2 wt. % WG at pH 11. The beaker was immediately dipped in a 50° C. pre-heated water bath while stirring. The suspension gradually changed colour from yellow to dark blue after ca. 5 min. The WG/G suspension was left to react for 2 h. After this, the suspension was cooled to RT and the acylation proceeded as previously described. This sample was designated WG/4G/25ED.

In a second experiment, the acylation of WG followed as described above, but before the cleaning of unreacted ED salts, the suspension temperature was raised to 50° C. while stirring in a pre-heated water bath, and 4 wt. % (WG mass basis) of G was added. The reaction continued for 2 h. The colour of the suspension changed to brown after 1.5 h of reaction. Thereafter, a cleaning was performed as described above. This sample was named 2WG/ED/G.

3.3 Analyses

Analyses of the material were performed as described in example 1.

3.4 Results

Figure 4A:
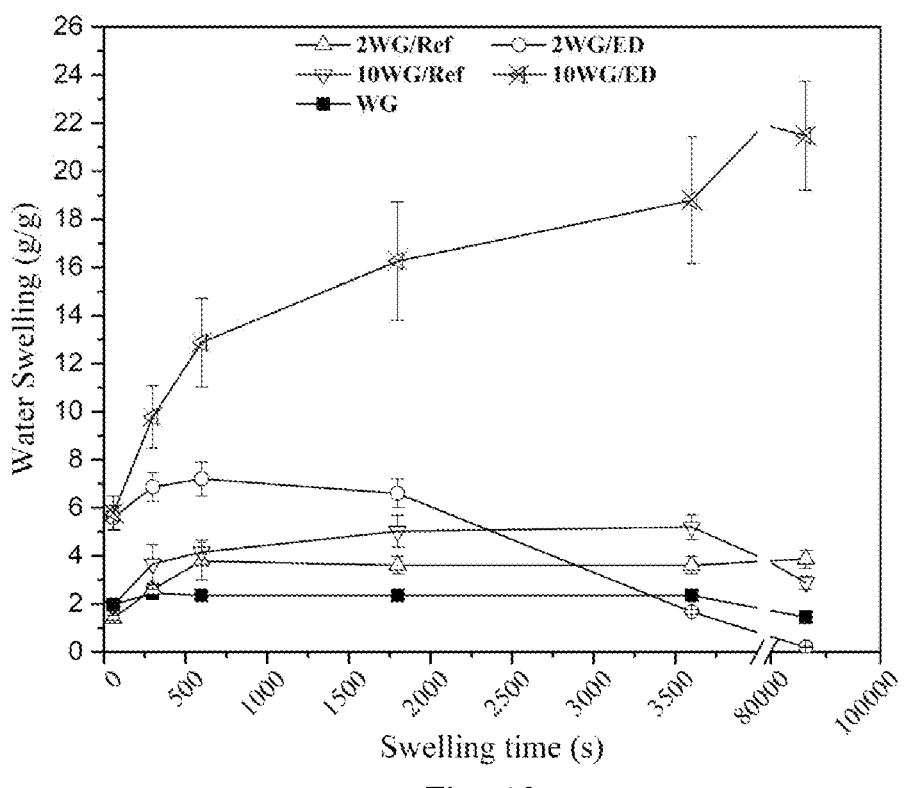
FIG. 4A shows FSC results obtained in example 3 at different protein concentrations in water, with/without ED.

The functionalization of the WG concentrates by using dilute protein suspensions (2WG/ED, 2 wt. %) led to particles that were not staying within the test bag but leaking out/dissolving in the MQw after the first 10 min, see FIG. 4A. Instead, the reference WG particles 2WG/Ref (which were not acylated) did not show any apparent leakage as the maximum swelling in MQw reached less than 4 g/g and kept stable during the entire test. Accordingly, the ED-treatment in the 2 wt. % WG protocol increases the gluten stability in water to a level that does not allow the protein to form a stable network that can expand and hold water without dissolving to a large extent.

In contrast 10WG/ED (10 wt. %) showed a water uptake of ca. 16 g/g and maximum of 22 g/g after 30 min and 24 h swelling, respectively. This represents a water swelling improvement of about 167%-200% relative to the reference sample at 10 wt. %, and the highest water uptake so far reported for WG particulate materials.

Figure 4B:
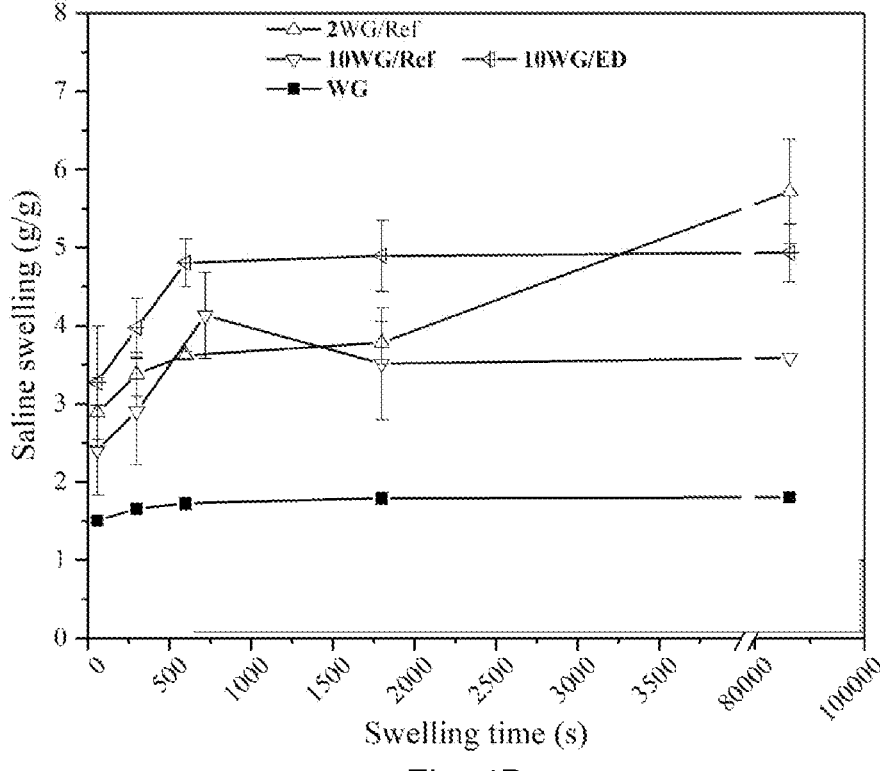
FIG. 4B shows FSC results obtained in example 3 at different protein concentrations in 0.9 wt. % saline solution.
Figure 4C:
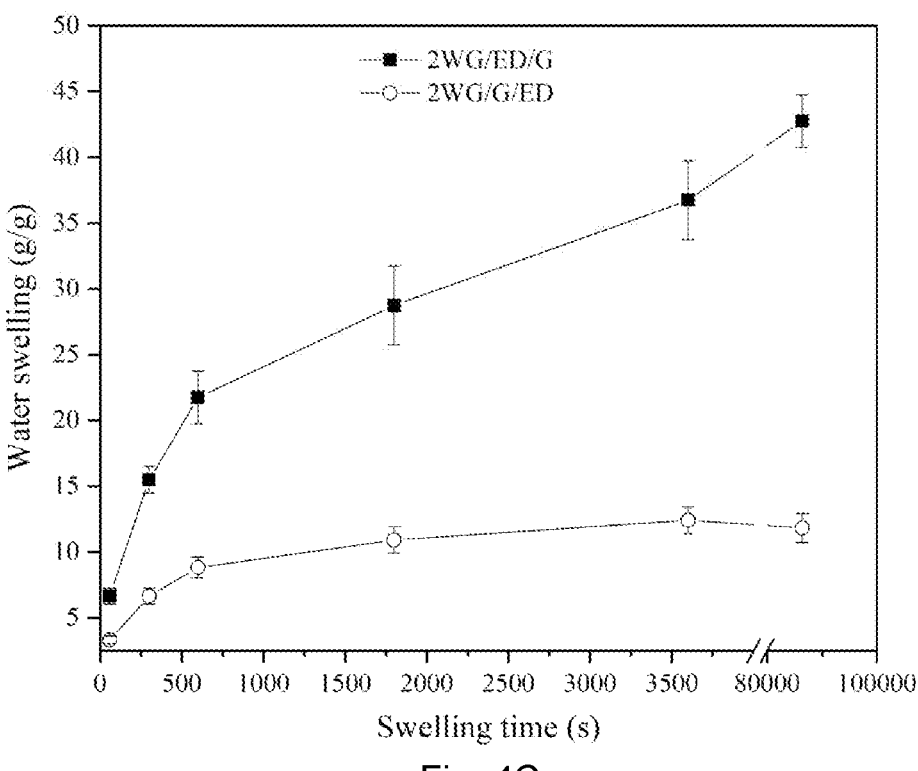
FIG. 4C shows FSC results obtained in example 3 using genipin before or after the acylation.

The 0.9% NaCl swelling, see FIG. 4B, showed that 10WG/ED can reach a maximum uptake of 5 g/g within 10 min. The CRC (g/g) values were WG:1.52; 2WG/Ref: 1.37; 10WG/Ref: 1.41; 10WG/ED: 2.11. The CRC values for the treated WG particles, here 10WG/ED were increased 35% compared to WG, with 2.11 g/g or ca. 250%, thus indicating that 50% of the saline solution is held within the treated-WG network. Overall, the MQw, and saline absorption capacity of these samples were low compared to the absorption capacity measured for commercial SAP used in diapers. Yet, the fast absorption and MQw/saline uptake obtained allow the material to be considered within superabsorbent polymer ranges thus having the potential to be used in applications where such SAP polymers are demanded. The functionalization process did not change the relative extractable PP (polymeric protein) and PM (monomeric protein) fractions in the 10WG/ED (10 wt. %) compared to the as-received WG, being approximately 50/50.

The material loss observed in the FSC of the 2WG/ED sample (2 wt. %) was confirmed with the extractable high molecular weight protein fraction (PP) being ca. 80%. This high PP extractability in 2WG/ED (not observed for 2WG/Ref) is associated with a less aggregated and more soluble protein network.

To confirm that the Low Concentration (LC) route was not damaging the WG network when using ED, SE-HPLC was performed on dried protein powders extracted after each experimental step. Additionally, to make sure that the aggregated state of the as-received commercial WG was not influencing the functionalization process, mildly extracted WG (WGm) was also studied in the HPLC following the same functionalization route as for 2WG/ED. Results are shown below in table 5.

TABLE 5

| SE-HPLC results (percentages for WG based materials are relative to as received WG and for WGM based materials as produced WGm) | | | | | |
|---|---|---|---|---|---|
| Sample | Total PP % | Total MP % | Ext1% | Ext2% | Ext3% |
| WG | 53 | 47 | 55 | 22 | 23 |
| WG/pH12 | 56 | 44 | 81 | 11 | 8 |
| WG/pH12/90° C. | 60 | 40 | 51 | 10 | 39 |
| WG/pH12/90° C./ED | 65 | 35 | 76 | 19 | 5 |
| WG/pH12/90° C./ED/Clean | 78 | 22 | 65 | 28 | 7 |
| WGm | 55 | 45 | 43 | 27 | 30 |
| WGm/pH12 | 57 | 43 | 70 | 15 | 15 |
| WGm/pH12/90° C. | 70 | 30 | 48 | 28 | 24 |
| WGm/pH12/90° C./ED | 62 | 38 | 79 | 18 | 3 |
| WGm/pH12/90° C./ED/Clean | 70 | 30 | 94 | 5 | 1 |

TABLE 5-continued

| SE-HPLC results (percentages for WG based materials are relative to as received WG and for WGM based materials as produced WGm) | | | | | |
|---|---|---|---|---|---|
| Sample | Total PP % | Total MP % | Ext1% | Ext2% | Ext3% |
| 2WG/Ref | 44 | 56 | 80 | 60 | 30 |
| 2WG/ED | 78 | 22 | 78 | 32 | 8 |
| 10WG/Ref | 56 | 44 | 20 | 30 | 50 |
| 10WG/ED | 52 | 48 | 42 | 16 | 28 |

Both the modified WGm and WG samples had approximately the same extraction profiles. WGm treated under alkali and 90° C. conditions gave a higher polymeric protein extraction (PP) than the WG sample, 70% vs 60% respectively. The functionalization process increases the amount of extracted polymeric fraction (PP) and that the fractions are extracted mainly in the first extraction, indicating an increase in protein solubility/extractability, which corresponds to the aim behind the ED treatment, i.e. increasing the proteins affinity to water.

Overall, the detailed analysis of the reaction steps and the comparison between WGm and WG does not indicate protein depolymerisation/damage to the WG structure due to the ED treatment. Hence, the increase in solubility/extractability observed for 2WG/ED and the highest total extraction (Ext. 1) for both 2WG/ED and 2WG/Ref shows that the increase in the protein concentration to at least 10 wt. % is preferred for giving an efficient balance between functionalization and network formation for producing highly swellable WG particles that are cohesive and do not dissolve.

The results for adding genipin, see FIG. 4D, showed that the adding genipin before acylation (2WG/G/ED) yielded a maximum of 15 g/g of water swelling, in contrast to when genipin was added after acylation (2WG/ED/G) which yielded a maximum of about 45 g/g of water swelling. Interestingly, the addition of genipin both prevented the material loss which was otherwise present for the 2 wt. % WG samples, and it also increased the swelling capacity.

The invention claimed is:

1. An absorbent article for absorption of body fluids, comprising an absorbent member that comprises at least one non-crosslinked plant protein based absorbent material comprising plant protein, wherein said plant protein is aggregated and acylated, and wherein said at least one non-crosslinked plant protein based absorbent material is obtainable by a method comprising steps of i. providing a mixture or suspension comprising a liquid and a plant protein, wherein said plant protein is sufficiently aggregated so as to be insoluble in the liquid, ii. acylating said plant protein by adding an acylating agent thereto, and iii. obtaining said at least one non-crosslinked plant protein based absorbent material.

2. The absorbent article according to claim 1, wherein the absorbent article is selected from the group of disposable hygiene absorbent products and medical dressings.

3. The absorbent article according to claim 1, wherein said absorbent member is disposed between a first liquid permeable layer and a second layer, or the absorbent member is wrapped in a liquid permeable wrapping.

4. The absorbent article according to claim 1, wherein in said method, said liquid is an aqueous liquid.

5. The absorbent article according to claim 1, wherein in said method, the content of plant protein in said mixture or suspension is from 2 wt. % to 10 wt. %.

6. The absorbent article according to claim 1, wherein in said method, the content of said plant protein in said mixture or suspension is from 10 wt. % to 40 wt. %.

7. The absorbent article according to claim 1, wherein in said method, said step (iii) of obtaining said at least one non-crosslinked plant protein based absorbent material comprises centrifuging a reaction mixture obtained from the step (ii) of acylating said plant protein.

8. The absorbent article according to claim 1, wherein in said method, the content of plant protein in said mixture or suspension is from 10 wt. % to 40 wt. %, and wherein said step (iii) of obtaining said at least one non-crosslinked plant protein based absorbent material comprises dispersing said acylated plant protein in an aqueous solution, after step (ii) and allowing it to dry.

9. The absorbent article according to claim 1, wherein in said method, said step (iii) of obtaining said at least one non-crosslinked plant protein based absorbent material comprises lyophilizing said plant protein after step (ii), or drying said plant protein after step (ii).

10. The absorbent article according to claim 1, wherein in said method, said step (iii) of obtaining said at least one non-crosslinked plant protein based absorbent material comprises oven-drying, drum-drying, spray-drying, freeze drying, fluid bed drying, microwave drying, microwave-vacuum drying, vacuum oven drying, shelf drying or flash-drying said plant protein after step (ii).

11. The absorbent article according to claim 1, wherein said method further comprises heat denaturing the plant protein at a temperature of at least 80° C. prior to step (ii).

12. The absorbent article according to claim 1, wherein said method does not include any step of crosslinking said plant protein using a crosslinker.

13. The absorbent article according to claim 1, wherein said method further comprises the step of adding genipin to the plant protein.

14. The absorbent article according to claim 1, wherein said plant protein comprises potato protein.

15. The absorbent article according to claim 1, wherein in said method, wherein said plant protein is obtained from an industrial process stream.

16. The absorbent article according to claim 15, wherein said industrial process stream is obtained from a starch extraction process, and wherein said industrial process stream is obtained directly after a starch extraction step.

17. The absorbent article according to claim 1, wherein the absorbent member comprises from 5 to 100% by weight of the at least one non-crosslinked plant protein based absorbent material.

18. The absorbent article according to claim 1, wherein the absorbent member comprises a mixture of said at least one non-crosslinked plant protein based absorbent material and a cross-linked acrylic acid-based super absorbent polymer.

19. The absorbent article according to claim 1, wherein the absorbent member comprises a mixture of said at least one non-crosslinked plant protein based absorbent material and fibrous material.

20. An absorbent article for absorption of body fluids, comprising an absorbent member, wherein the absorbent member comprises at least one non-crosslinked plant protein based absorbent material comprising plant protein, wherein the plant protein is aggregated and acylated, and wherein the at least one non-crosslinked plant protein based absorbent material has a free swelling capacity (FSC) of at least 3 g of 0.9 wt. % NaCl solution per gram absorbent material at 10 seconds.

21. The absorbent article according to claim 20, wherein said at least one non-crosslinked plant protein based absorbent material is obtainable by a method comprising steps of i. providing a mixture or suspension comprising a liquid and a plant protein, wherein said plant protein is insoluble in the liquid, ii. acylating said plant protein by adding an acylating agent thereto, and iii. obtaining said at least one non-crosslinked plant protein based absorbent material.

\*   \*   \*   \*   \*